United States Patent [19]

Clarke

[11] Patent Number: 5,383,877
[45] Date of Patent: Jan. 24, 1995

[54] INSTRUMENTS AND METHOD FOR SUTURING AND LIGATION

[76] Inventor: Henry C. Clarke, 1558 Victoria Avenue, Windsor, Ontario, Canada, N8Y 1PS

[21] Appl. No.: 958,548

[22] Filed: Oct. 8, 1992

Related U.S. Application Data

[63] Continuation of Ser. No. 694,114, May 1, 1991, abandoned.

[51] Int. Cl.⁶ ............................................. A61B 17/00
[52] U.S. Cl. .................... 606/148; 606/139; 606/207
[58] Field of Search ............... 606/139, 144, 148, 205, 606/206, 207

[56] References Cited

U.S. PATENT DOCUMENTS

| | | | |
|---|---|---|---|
| 671,337 | 4/1901 | Gibson | 606/148 |
| 3,763,860 | 10/1973 | Clarke | 128/334 |
| 3,871,379 | 3/1975 | Clarke | 606/148 |
| 5,100,421 | 3/1992 | Christoodias | 606/147 |

OTHER PUBLICATIONS

M. M. Gazayerli, M.D., D.S. "The Gazayerlie Knot—Tying Instrument or Ligator for Use in Diverse Laparoscopic Surgical Procedures"—1991—pp. 254–258.

Primary Examiner—Stephen C. Pellegrino
Assistant Examiner—Jeffrey A. Schmidt
Attorney, Agent, or Firm—Barnes, Kisselle, Raisch, Choate, Whittemore & Hulbert

[57] ABSTRACT

A laparscopic method and instrument for suturing and ligation of tissue in a body cavity of a patient through trocar tubes inserted into the cavity. First forceps have a needle on the end of a movable jaw to pierce the tissue and pass a surgical thread through it. Second forceps have a movable jaw and a groove through the ends of both jaws and transverse to the pivotal axis of the movable jaw for advancing a loose tie in the surgical thread through a trocar tube and into engagement with the tissue and tensioning or drawing up the tie to close the tissue and produce a secure knot. Preferably, the jaws of both forceps each have therein a groove for guiding the thread to avoid tearing the tissue and blades for cutting the excess thread when the suture is completed.

17 Claims, 3 Drawing Sheets

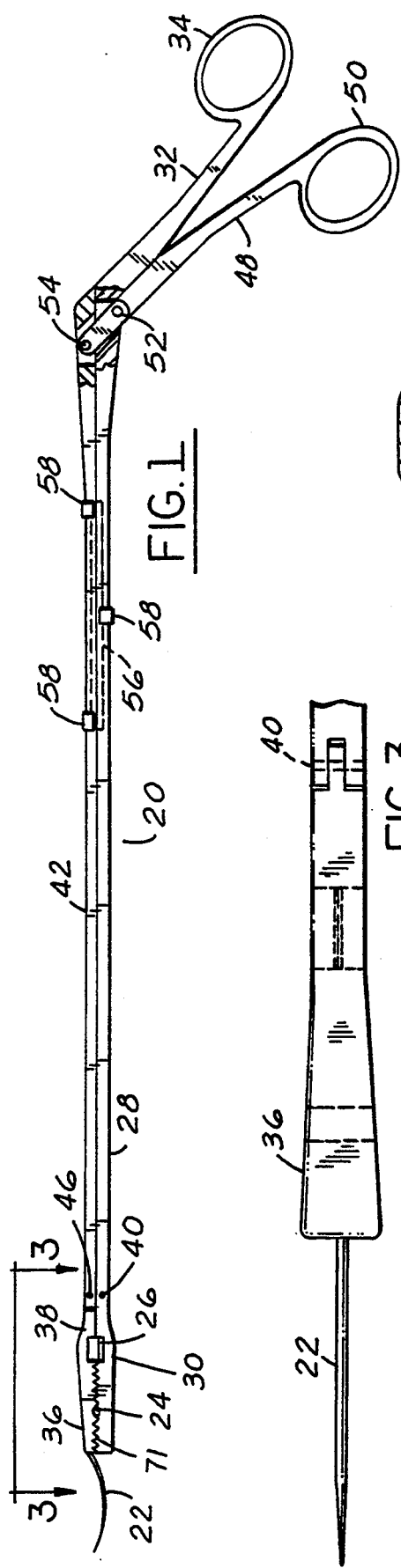
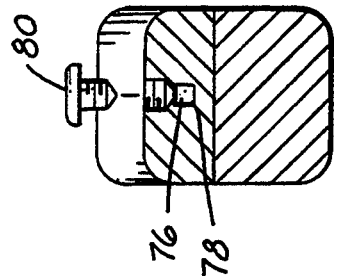
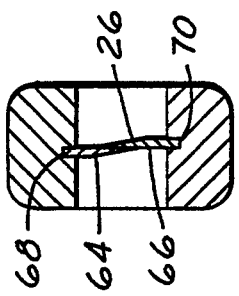
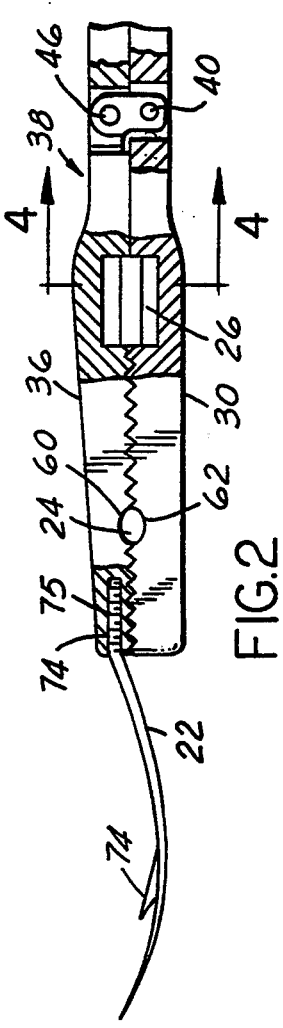
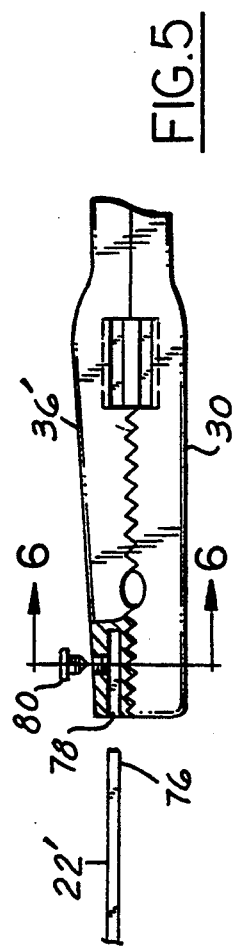

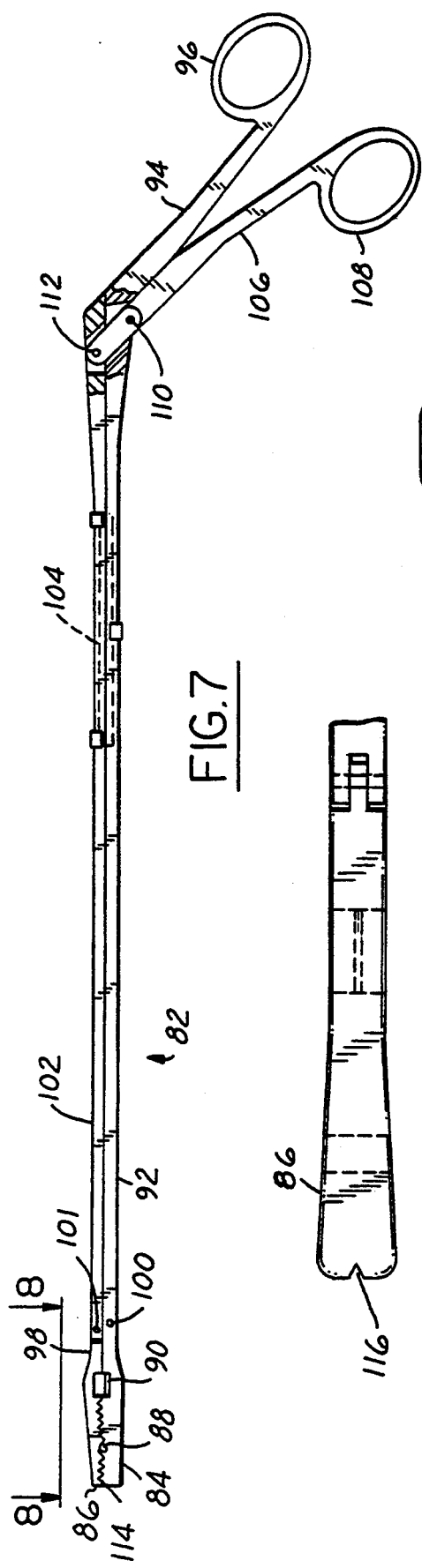
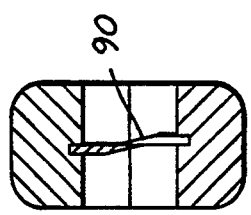
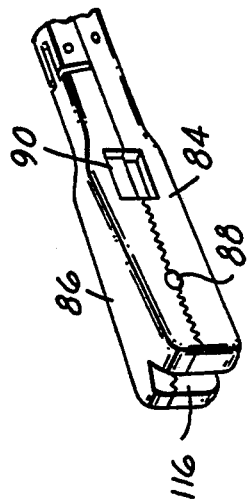
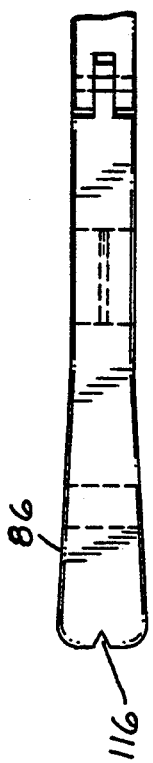
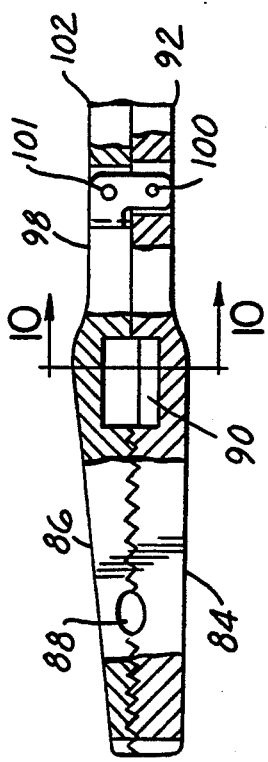

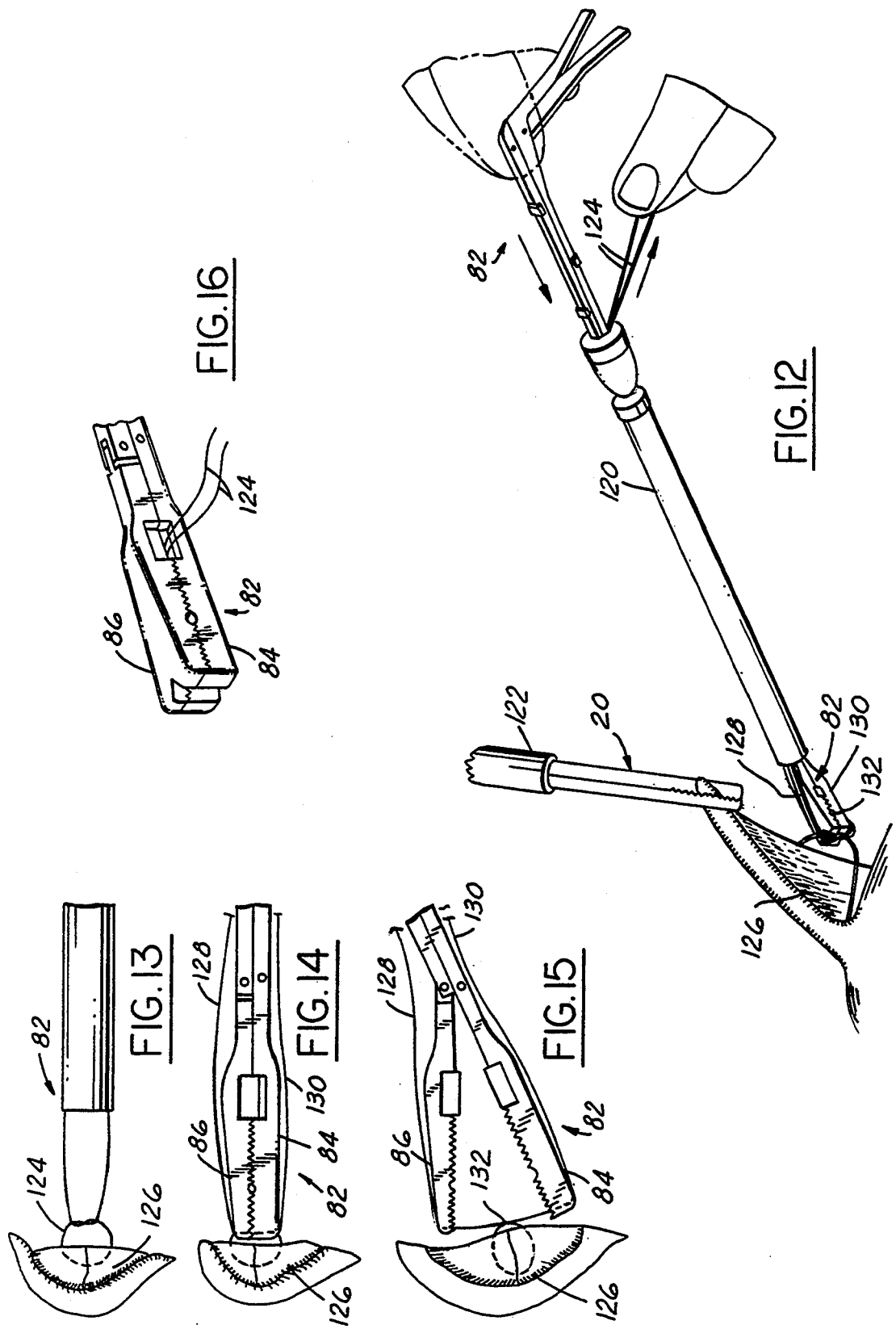

INSTRUMENTS AND METHOD FOR SUTURING AND LIGATION

This is a continuation of copending U.S. application Ser. No. 07/694,114, filed on May 1, 1991, now abandoned.

FIELD OF THE INVENTION

This invention relates to laparoscopic instruments and methods for suturing and ligation.

BACKGROUND

Laparoscopy is a technique for performing surgery in body cavities, such as an abdomen, without making a major incision or opening. Two or more spaced apart small openings are made in the body and trocar sheaths or tubes are inserted through each opening. Various instruments are then inserted through these tubes to perform the surgery.

Examples of the types of operations performed are: biopsy and electrocoagulation; lysis of adhesions with electrocoagulation; ovarian follicle aspiration; biopsy of the ovary; ovarian cyst aspiration; electrocoagulation of bleeding points such as bleeding corpus luteum; biopsies in general; and excision of small tumors with electrocoagulation.

In some of these procedures, difficulties have been encountered when blood vessels are cut and bleeding occurs. This complicates the procedure and may endanger the patient because of the prior inability to suture and ligate with laparoscopic procedures.

Accordingly, instruments and methods have been previously developed for performing laparoscopic procedures such as those disclosed in U.S. Pat. Nos. 3,871,379 and 3,763,860. These methods require at least three different instruments to perform the laparoscopic procedure. These instruments usually include a first combined laparoscopic needle and forceps, a second combined laparoscopic tissue forceps, suture guide and cutter, and a third laparoscopic ligator.

Generally, the first and second forceps are manipulated to pierce portions of tissue, pass the suture through the tissue and withdraw both ends of the suture through one trocar to the exterior of the body. Then outside of the body the free ends of the suture are tied together to form a loose tie to ligate the tissue. The loose tie is then introduced by a third instrument, usually a ligator, through the associated trocar sheath, down to the central portion of the suture to secure the tie. After the tie is tensioned to produce a knot, the third ligator is withdrawn from its associated trocar tube. These steps are repeated for each stitch needed to ligate the tissue. Then the second forceps is reinserted into the associated trocar tube to cut the free ends of the suture to complete the procedure.

It is extremely important in procedures of this type to avoid tearing the tissue, to be able to adequately tension or draw each tie snugly up to the tissue to prevent subsequent bleeding and, to complete the ligation process as quickly as possible. Unfortunately, it is cumbersome to use these three instruments to snugly tie each stitch.

SUMMARY

For tying each stitch of a suture, forceps with a pair of jaws at one end pivotally movable to closed and open positions have a groove in the distal or free ends of the jaws for inserting a tie in a suture thread through a trocar and drawing it snugly or securely around body tissue. This groove is transverse to both the longitude of the forceps and the pivot axis of its jaws. Preferably, to minimize the risk of damaging the tissue while pulling the thread through it, the jaws also have a slot between them through which the thread can pass when the jaws are closed. Preferably, to sever the thread, the jaws also have cutter blades.

In the method for suture ligating, a first forceps with jaws having the transverse groove and preferably the slot and a cutter blade is inserted through a trocar into a cavity of a patient's body. A second forceps with a needle and suture thread is also inserted into the cavity through another trocar. The second forceps is manipulated to pierce the tissue to be ligated and pass the thread through it. The first forceps is manipulated to grasp and remove the thread from the needle and then to dispose it in the slot of this forceps. The second forceps is manipulated to pull one end of the thread from the tissue through the same trocar through which the other end of the thread extends. The first forceps is also removed from the other trocar. A loose tie is placed in the thread. With the jaws closed of the first forceps, the tie is placed in the transverse groove and fed through the trocar to the tissue. While maintaining tension on the free ends of the thread (exteriorly of the trocar), the jaws of the first forceps are opened to thereby draw the tie firmly or snugly up to the tissue to quickly provide a proper knot and stitch. These steps are repeated as needed to provide the number of stitches desired to ligate the tissue. Then the free ends of the suture thread are cut preferably by the first forceps.

Objects, features and advantages of this invention include increasing the ease, speed and ability to suture and ligate in laparoscopy, improving the tying of stitches, and a procedure requiring fewer steps and instruments.

BRIEF DESCRIPTION OF THE DRAWINGS

These and other objects, features and advantages of this invention will be apparent from the following detailed description, appended claims and accompanying drawings in which:

FIG. 1 is a side elevational view of laparoscopic needle forceps with a suture guide and cutter.

FIG. 2 is a fragmentary side view with portions broken away of the instrument of FIG. 1.

FIG. 3 is an enlarged fragmentary top plan view taken substantially along lines 3—3 of FIG. 1.

FIG. 4 is a cross sectional view taken along line 4—4 of FIG. 2.

FIG. 5 is a fragmentary side view showing a second embodiment of the needle attachment.

FIG. 6 is a cross sectional view taken along the line 6—6 of FIG. 5.

FIG. 7 is a side elevational view of laparoscopic ligator forceps with a suture thread guide and cutter.

FIG. 8 is an enlarged fragmentary top plan view taken along the line 8—8 of FIG. 7.

FIG. 9 is an enlarged fragmentary side view partially in section of the instrument of FIG. 7.

FIG. 10 is a cross section taken along the line 10—10 of FIG. 9.

FIG. 11 is a fragmentary perspective view of the instrument of FIG. 7.

FIG. 12 is a semi-schematic and perspective view of trocar tubes and the ligator forceps used to tie a knot in a suture thread in tissue in a cavity of a patient.

FIG. 13 is a fragmentary side view of a loose tie after insertion through its associated trocar.

FIG. 14 is a fragmentary side view of the laparoscopic ligator forceps urging a loose tie in a surgical thread toward tissue to be sutured.

FIG. 15 is a fragmentary side view of the ligator forceps of FIG. 13 with the jaws in the open position to fully tighten the tie into a secure knot.

FIG. 16 is a fragmentary perspective view of the ligator forceps being used to cut a surgical thread.

DETAILED DESCRIPTION

FIGS. 1–6 illustrates forceps 20 with a needle 22, guide 24 and cutters 26 for a suture thread. The forceps have an elongate slender link 28 with a fixed jaw 30 on one end and a handle 32 on the other end with a finger ring 34. A movable jaw 36 with an integral lever arm 38 is pivotally mounted on the link 28 by a pin 40. A movable elongate link 42 is slidably received on the link 28 and at one end pivotally connected to the movable jaw by a pin 46. An actuator handle or arm 48 with a finger ring 50 is pivotally mounted on the link 28 by a pin 52 and pivotally connected to the movable link 42 by a pin 54. The links are releasably retained together in longitudinal sliding relationship by a spring clip 56 with tabs 58 which encircle and engage the links. The links 28 & 42, and arms 32 & 48 provide a parallelogram linkage arrangement so that in use of the forceps 20 the jaws 30 & 36 are closed by squeezing the handles 32 & 48 together and opened by pivotally moving the handles apart.

The guide 24 for the suture thread is provided by grooves 60 & 62 in the jaws which when closed form a through hole in which the thread can be received. The grooves 60 & 62 are in the gripping faces of the jaws and extend parallel to the pivot axis of the movable jaw. The cutter 26 for the suture thread has a pair of complementary shear blades 64 & 66 with knife edges which overlap when the jaws are closed. The blades are received in recesses 68 & 70 in the jaws. Preferably, the gripping surfaces of each jaw have serrations 71 therein.

The needle 22 has a protuberance or barb 72 or preferably an eye for receiving a suture thread and a threaded shank portion 74 for removably attaching the needle to the end of the movable jaw. The needle shank 74 is received in a complementary threaded blind hole 75 in the end of the jaw 36. FIGS. 5 and 6 illustrate a needle 22' with a plain shank 76 with a square cross section removably received in a complementary blind hole 78 in the movable jaw 36' and releasably secured therein by a set screw 80. Preferably, the needles 22 & 22' are disposable.

In use, the forceps 20 can perform several functions, including manipulating the needle 22 to pierce the tissue and pass a suture thread therethrough, protecting the tissue as the thread is pulled through the tissue, cutting the thread, and gripping and releasing the thread, tissue, etc.

FIGS. 7–11 illustrate a forceps 82 of this invention with jaws 84 & 86 for guiding and tensioning ties in a suture thread, and a guide 88 and cutter 90 for suture thread. The forceps have an elongate link 92 with the jaw 84 fixed on one end and an extension handle 94 with a finger ring 96 on the other end. The movable jaw 86 has an integral arm 98 pivotally connected to the link 92 by a pin 100. An elongate movable link 102 is slidably received and releasably retained on the other link 92 by a spring clip 104 and pivotally connected at one end to the movable jaw 86 by a pin 101. A movable arm or handle 106 with a finger ring 108 is pivotally mounted by a pin 110 on the link 92 and pivotally connected to the other end of the movable link 102 by a pin 112. Preferably, to facilitate gripping tissue, thread and the like the jaws have serrations 114. The links 92 & 102 and arms 98 & 106 provide a parallelogram linkage arrangement so that in use of the forceps 82, the jaws 84 & 86 are closed by squeezing the handles together and opened by pivotally moving the handles apart.

To facilitate guiding and tensioning ties in suture thread, a groove 116 is provided in the free ends of the jaws 84 & 86. This groove extends through the ends of the jaws transverse to the axis about which the movable jaw 86 pivots. In use, portions of the runs of the thread of a suture are received in the groove 116 for guiding the ties through a trocar tube and in cooperation with opening of the jaws, tensioning the loose tie to draw it and the adjacent tissue together and form a secure knot.

If desired, the forceps 82 can be constructed so that both jaws are pivotally movable. For example, both jaws can be pivoted on one link and connected through arms to the other link. Each arm is pivoted at one end to one jaw and both arms are pivoted at the other end to the other link so that the jaws are moved in unison to open and closed positions by relative movement of the links 92 & 102.

In use, the forceps 82 can perform several functions, including protecting tissue as a suture thread is pulled through it, moving loose ties through a trocar and into position adjacent the tissue which is being sutured, tensioning loose ties to produce a secure knot, cutting the thread, and gripping and releasing the thread, tissue, etc.

Larparacopy procedures may be performed with the forceps 20 & 82 in the following manner. First two sheath trocars 120 & 122 are inserted into a cavity in the patient's body at spaced apart locations. The needle 22 of the forceps 20 is threaded with a suitable surgical thread 124 in the usual manner and then the forceps are inserted through the trocar 120 with one end of the thread 124 retained externally of the trocar. The handles of the forceps 20 are manipulated to open the jaws so that the needle 22 extends generally transversely of the forceps to facilitate piercing the tissue 126. The forceps 20 are manipulated to pierce the tissue with the needle 22 and to pass the thread therethrough. The forceps 82 are inserted through the trocar 122 and then manipulated to grasp the end of the thread and disengage it from the needle 22. The forceps 20 are then manipulated to withdraw the needle 22 from the tissue and then to grip the free end of the thread which is thereafter released by the forceps 82. Preferably, the forceps 82 are then manipulated to enclose and dispose the thread in the guide 88 of the forceps 82 to prevent the tissue from being subjected to force or pulled and possibly being torn as the free end of the thread is pulled through the trocar 120 by removing the forceps 20 from the trocar. This results in both runs of the thread extending through the trocar 120 to the exterior thereof.

A loose tie is manually made in the thread outside of the trocar 120. With the jaws closed the loose tie is disposed in the groove 116 in the jaws of the forceps 82 with the runs 128 & 130 of the thread extending over the exterior of the jaws and along the length of the forceps. With the jaws closed the forceps 82 are inserted through the trocar 120 and manipulated to move the loose tie 132 through the trocar, as shown in FIG. 12 and immediately adjacent the tissue, as shown in FIGS. 13 and 14. After the loose tie is disposed in the desired position (as shown in FIG. 14), the handles of the forceps 82 are manipulated to open the jaws 84 & 86 (as shown in FIG. 15), while maintaining tension on the free ends of the thread exteriorly of the trocar to thereby draw the tie firmly to the tissue (and draw tissue together) and to tighten the tie to form a secure knot. After the knot is secured, the forceps 82 are manipulated to close its jaws and withdraw it. This procedure may be repeated to provide as many additional ties and/or stitches as is desired to completely suture the incision or opening in the tissue. After the suture is completed, the forceps 82 may be manipulated to cut off or trim the excess thread which is then removed through its associated trocar tube. Thereafter, all of the forceps and the trocar tubes are removed.

Since either of the forceps 20 and 82 can perform the functions of gripping, guiding, protecting tissue, and cutting thread, the number of times instruments must be removed and reinserted through the trocar tube is reduced. Moreover, the forceps 82 decreases the number of instruments required to perform laparoscopic suturing and ligation procedures and readily and easily produce secure knots and draw tissue together.

I claim:

1. A method for suture ligating using laparoscopic instruments comprising:
   a) inserting at least first and second trocars at spaced locations into the body of a patient,
   b) inserting through the first trocar a first laparoscopic forceps having jaws and a needle threaded with a surgical thread with one end or the thread adjacent the needle and with a portion of the thread extending through the first trocar and the other end of the thread being retained exteriorly of the first trocar,
   c) inserting through the second trocar a second laparoscopic forceps having jaws with a groove through outer free ends of the jaws extending transverse to the longitude of the second forceps and the pivotal axis of the jaws,
   d) manipulating the first forceps to pierce the tissue with the needle and bring a free end of the thread therethrough,
   e) manipulating the second forceps and jaws thereof to grasp the thread adjacent the free end and disengage the thread from said needle,
   f) manipulating the first forceps to remove the needle from the tissue and then to grasp the thread adjacent its free end within the jaws of the first forceps,
   g) withdrawing said first forceps through said first torcar to bring said free end of the thread through and outside of said first trocar,
   h) tying the runs of the thread together to provide a loose tie exteriorly of the first trocar,
   i) withdrawing the second forceps from the second trocar,
   j) manipulating the second forceps with its jaws in their closed position and the runs of the thread adjacent such loose tie being received in such groove to move said loose tie through the first trocar and immediately adjacent the tissue, and
   k) manipulating the said second forceps to move its jaws to an open position while maintaining the runs of the suture thread taut to finally tighten the tie into a secure knot to hold the tissue together.

2. The method as claimed in claim 1 further comprising after step (k) cutting the ends of the suture with shear blades secured in the jaws of the second forceps.

3. The method as claimed in claim 1 further comprising after step (k) removing said second forceps from said first trocar.

4. The method as claimed in claim 1 further comprising after step (f) and before step (g) disposing such thread through a guide groove between the jaws of said second forceps and encircling such thread by closing the jaws of said second forceps.

5. The method as claimed in claim 1 further comprising after step (f) and before step (g) disposing such thread through a guide groove between the jaws of said second forceps and encircling such thread by closing the jaws of said second forceps to thereby prevent the thread from tending to pull on and tear the tissue while withdrawing the first forceps through the first trocar to bring such free end of the thread through and outside of the first trocar, and after step (g) and before step (i) opening the jaws of said second forceps and releasing such thread from such guide groove thereof.

6. A method for suture ligating using laparoscopic instruments comprising:
   a) inserting at least a first trocar into the body of a patient,
   b) inserting through the first trocar a first laparoscopic forceps having jaws and a needle threaded with a surgical thread with one free end of the thread adjacent the needle and with a portion of the thread extending through the first trocar and the other end of the thread being retained exteriorly of the first trocar,
   c) manipulating the first forceps to pierce the tissue with the needle and bring the one free end of the thread therethrough,
   d) disengaging the thread from the needle,
   e) manipulating the first forceps to remove the needle from the tissue and then to grasp the thread adjacent the free end of the thread within the jaws of the first forceps,
   f) withdrawing said first forceps through said first trocar to bring such free end of the thread through and outside of said trocar,
   g) tying the runs of the thread together to provide a loose tie exteriorly of the first trocar,
   h) providing outside the first trocar a second laparoscopic forceps having a pair of jaws at least one of which pivots about an axis transverse to the longitude of the second forceps and with a groove through the outer ends of the jaws and extending at generally a right angle to both said axis and the longitude of the second forceps,
   i) manipulating the second forceps with its jaws in their closed position and the runs of the thread adjacent said loose tie being received in said groove to move said loose tie through the first trocar, and
   j) manipulating the second forceps to move its jaws to an open position and tensioning the runs of the suture thread to finally tighten said tie to hold the tissue together.

7. The method as claimed in claim 6 further comprising after step (j) cutting the ends of the suture with shear blades secured in the jaws of the second forceps.

8. The method as claimed in claim 6 further comprising after step (j) removing said second forceps from said first trocar.

9. The method as claimed in claim 6 further comprising, inserting a second trocar into the body of the patient at a location spaced from the first trocar, inserting a second forceps through said second trocar, and after step (e) and before step (f) disposing said thread through a guide groove between the jaws of said second forceps and encircling said thread by closing the jaws of said second forceps while performing step (f).

10. The method as claimed in claim 6 further comprising inserting a second trocar into the body of the patient at a location spaced from the first trocar, inserting a second foreceps through said second trocar, and after step (e) and before step (f) disposing said thread through a guide groove between the jaws of said second forceps and encircling said thread by closing the jaws of said second forceps to thereby prevent the thread from tending to pull on and tear the tissue while withdrawing the first forceps through the first trocar to bring said free end of said thread through and outside of the first trocar, and after step (f) and before step (h) opening the jaws of said second forceps and releasing said thread from said guide groove thereof.

11. A laparoscopic forceps for extending through a trocar in the body of a patient and positioning and tensioning a loose tie in a suture thread within the body of a patient and having both runs of the thread passing through the trocar to the exterior thereof for manual engagement by a user of the forceps, the laparoscopic forceps comprising:
a pair of elongated slender links which lie in side by side relationship and are constructed and arranged to be received in the trocar tube,
a pair of jaws adjacent one end of said elongated links and carried by at least one of said links,
at least one of said jaws being pivotally movable to open and closed positions relative to the other jaw about an axis extending transversely to the longitude of the forceps, said jaws being constructed and arranged so that in the closed position they can pass through the trocar tube and into the body of the patient,
means for manually moving said jaws to a closed position and to an open position, and
a groove through the free ends of both jaws and extending at generally a right angle to both the longitude of the forceps and the axis of pivotal movement of said jaws and opening outwardly of the jaws, said groove being constructed and arranged for slidably receiving the runs of the suture thread with a loose tie therein adjacent the free ends of the jaws and with the runs of the thread extending from both ends of such groove generally longitudinally along the elongated links of the forceps and through the trocar tube to the exterior thereof to facilitate tensioning of the tie by opening the jaws while in the body with the thread slidably received in the groove through both of said jaws.

12. The laparoscopic forceps as claimed in claim 11 wherein said jaws have shear blades secured therein inboard from the free ends thereof to provide a suture thread cutting action when the jaws move from the open to the closed position.

13. The laparoscopic forceps as claimed in claim 11 wherein said jaws have at least one suture thread guide groove therein inboard from the free ends thereof and extending axially generally parallel to said axis about which at least said one jaw pivots and constructed and arranged such that when said jaws are closed said suture guide groove provides an opening having a substantially continuous periphery through which the suture thread can be slidably received.

14. The laparoscopic forceps as claimed in claim 13 wherein said jaws have shear blades secured therein inboard from the free ends thereof to provide a suture thread cutting action when the jaws move from the open to the closed position.

15. A laparoscopic forceps for extending through a trocar in the body of a patient and positioning and tensioning a loose tie in a surgical thread within the body of a patient and having both runs of the thread passing through the trocar to the exterior thereof for manual engagement by a user of the forceps, the laparoscopic forceps comprising, at least one elongate slender element constructed and arranged to be received in the trocar tube, a pair of jaws adjacent one end of said elongate element and carried by said elongate element, at least one of said jaws being pivoted to move about an axis extending transversely to the longitude of said elongate element to open and closed positions relative to the other jaw of said pair of jaws, said jaws being constructed and arranged so that in the closed position they will pass through the trocar tube and into the body of the patient, means carried by said elongate element and manually engagable adjacent the end of said elongate element opposite said jaws for moving said jaws to a closed position and to an open position, and a groove through the free end of both jaws and extending at generally a right angle to both the longitude of said elongate element and said axis of pivotal movement of said at least one jaw and opening outwardly of said jaws, and said groove being constructed and arranged for slidably receiving the runs of the surgical thread with a loose tie therein adjacent the free ends of the jaws and with the runs of the thread extending from both ends of said groove generally longitudinally along said elongate element toward the other end of said elongate element and through the trocar tube to the exterior thereof to facilitate tensioning of the tie in the thread by opening said jaws while in the body with the thread slidably received in the groove through both of said jaws.

16. The laparoscopic forceps as claimed in claim 15 which also comprises at least one surgical thread guide groove through at least one of said jaws, inboard from the free ends of said jaws, and extending generally parallel to said axis of pivotal movement of said at least one jaw and constructed and arranged such that when said jaws are closed, said suture guide groove provides an opening having a substantially continuous periphery through which a surgical thread can be slidably received and retained therein and when said jaws are open the surgical thread is released from said guide groove.

17. The laparoscopic forceps as claimed in claim 15 wherein said jaws have shear blades secured therein inboard from the free ends of said jaws to provide a suture thread cutting action when said jaws are moved from the open to the closed position of said jaws.

* * * * *